US 7,101,680 B2

(12) United States Patent
Jackowski et al.

(10) Patent No.: US 7,101,680 B2
(45) Date of Patent: *Sep. 5, 2006

(54) METHOD FOR DETECTING THE PRESENCE OF MONOMERIC BRAIN ASSOCIATED HUMAN GLUTAMINE SYNTHETASE

(75) Inventors: George Jackowski, Kettleby (CA); Miyoko Takahashi, North York (CA)

(73) Assignee: Syn X Pharma, Inc., Ontario (CA)

(*) Notice: Subject to any disclaimer, the term of this patent is extended or adjusted under 35 U.S.C. 154(b) by 399 days.

This patent is subject to a terminal disclaimer.

(21) Appl. No.: 09/971,740

(22) Filed: Oct. 4, 2001

(65) Prior Publication Data

US 2002/0160425 A1    Oct. 31, 2002

Related U.S. Application Data

(63) Continuation of application No. 09/842,079, filed on Apr. 25, 2001, now Pat. No. 6,451,547.

(51) Int. Cl.
G01N 33/53 (2006.01)
G01N 33/573 (2006.01)
G01N 33/577 (2006.01)
C07K 16/40 (2006.01)

(52) U.S. Cl. ............ 435/7.4; 435/7.1; 530/387.1; 530/388.1; 530/388.26

(58) Field of Classification Search ............ 435/7.1, 435/7.4, 7.9, 7.92, 7.93, 7.95, 7.94; 530/387.2, 530/388.1, 388.25, 388.26, 389.1, 389.3, 530/391.1
See application file for complete search history.

(56) References Cited

U.S. PATENT DOCUMENTS 5,445,937 A   8/1995  Haley .................. 435/6
5,508,167 A   4/1996  Roses et al. .......... 435/6
6,451,547 B1* 9/2002  Jackowski et al. ..... 435/7.4

OTHER PUBLICATIONS

Boksha et al., "Glutamine Synthetase and Glutamine Synthetase-Like Protein from Human Brain: Purification and Comparative Characterization", Journal of Neurochemistry, vol. 75, No. 6, (2000), pp. 2574-2582.
Tumani et al., Glutamine synthetase in cerebrospinal fluid, serum, and brain, Arch. Neurol., (1999) 56, pp. 1241-1246.
Gunnersen et al., Detection of glutamine synthetase in the cerebrospinal fluid of Alzheimer diseased patients: A potential diagnostic biochemical marker, Proc. Natl. Acad.Sci., (1992) 89, pp. 11949-11953.
Hensley et al., A model for β-amyloid aggregation and neurotoxicity based on free radical generation by the peptide: Relevance to Alzheimer disease, Pro. Natl. Acad.Sci., (1994) 91, pp. 3270-3274.
Sheng et al., S100β protein expression in Alzheimer disease: Potential role in the phatogensis of neuritic plaques, J. of Neurosci. Res., (1994) pp. 398-404.
Mrak et al., Correlation of astrocytic S100β expression with dystrophic neurites in amyloid plaques of Alzheimer's disease, J. of Neuropathol. and Exp. Neurol., (1996) 55, 3, pp. 273-279.
Tumani et al., Purification and immunocharacterization of human brain glutamine synthetase and its detection in cerebrospinal fluid and serum by a sandwich enzyme immunoassay, J. of Immunol. Meth., (1995) 188, pp. 155-163.

* cited by examiner

*Primary Examiner*—Elizabeth Kemmerer
*Assistant Examiner*—Bridget E. Bunner
(74) *Attorney, Agent, or Firm*—McHale & Slavin, P.A.

(57) ABSTRACT

A method for diagnosing Alzheimer's disease(AD) is disclosed. The method involves directly detecting the presence of a biochemical marker, specifically human glutamine synthetase, in bodily fluid, preferably blood or a blood product. The detection is by an immunoassay incorporating an antibody specific to human glutamine synthetase. In addition, a method for distinguishing between AD and non-AD dementia is disclosed.

3 Claims, 3 Drawing Sheets

FIGURE 1

AD samples (Serum)

| Syn-X CODE | Age | Sex | S100B (ng/ml) Cut-off=0.02 | NSE (ng/ml) Cut-off=8.34 | GS (ng/ml) Cut-off=0.022 | History, Diagnosis : MMSE 20-30-mild 10-19 moderate 0 -9 severe |
|---|---|---|---|---|---|---|
| ADH-011 | 66 | M | 0.010 | 9.065 | 0.058 | 22 mild AD |
| ADH-012 | 79 | M | 0.008 | 4.253 | 0.023 | 14 moderate AD |
| ADH-013 | 76 | M | 0.005 | 6.166 | 0.068 | 17 moderate AD |
| ADH-014 | 85 | F | 0.009 | 4.784 | 0.162 | 17 moderate AD |
| ADH-015 | 81 | M | 0.011 | 8.608 | 0.058 | 25 mild AD |
| ADH-016 | 83 | F | 0.009 | 14.679 | 0.077 | 22 mild AD |
| ADH-017 | 84 | F | 0.015 | 10.724 | 0.092 | 22 mild AD |
| ADH-018 | 87 | F | 0.011 | 4.651 | 0.042 | 21 mild AD |
| ADH-019 | 74 | F | 0.010 | 6.211 | 0.131 | 22 mild AD |
| ADH-020 | 74 | M | 0.004 | 3.504 | 0.035 | 25 mild AD |
| ADH-021 | 77 | M | 0.006 | 1.888 | 0.045 | 20 mild AD |
| ADH-022 | 84 | M | 0.010 | 4.784 | 0.049 | 23 mild AD |
| ADH-023 | 79 | M | 0.009 | 7.698 | 0.052 | 27 mild AD |
| ADH-024 | 87 | M | 0.014 | 8.699 | 0.071 | 20 moderate AD |
| ADH-025 | 75 | F | 0.009 | 5.853 | 0.036 | 21 mild AD |
| ADH-026 | 79 | F | 0.006 | 6.750 | 0.043 | 24 mild AD |
| ADH-027 | 81 | M | 0.005 | 3.284 | 0.048 | 23 mild AD |
| ADH-028 | 54 | M | 0.006 | 4.121 | 0.022 | 21 mild AD / poss VaD |
| ADH-029 | 82 | F | 0.004 | 12.969 | 0.080 | 23 mild AD |
| ADH-030 | 81 | F | 0.009 | 4.563 | 0.048 | 24 mild AD |
| ADH-031 | 83 | F | 0.009 | 16.316 | 0.067 | 20 mild AD |
| ADH-032 | 84 | F | 0.017 | 3.460 | 0.029 | 24 mild AD |
| ADH-033 | 87 | F | 0.020 | 2.628 | 0.067 | 21 mild AD |
| ADH-034 | 74 | F | 0.022 | 9.111 | 0.070 | 22 mild AD |
| Sensitivity | | | 8 % | 33 % | 100 % | |

FIGURE 2

Non-AD Dementia Controls

DC-1

| Syn-X CODE | Age | Sex | S100B (ng/ml) Cut-off=0.02 | NSE (ng/ml) Cut-off=8.34 | GS (ng/ml) Cut-off=0.022 | History, Diagnosis |
|---|---|---|---|---|---|---|
| DC-001 | 86 | M | 0 | 3.816 | 0.019 | mild dementia |
| DC-002 | 69 | M | 0 | 3.816 | 0.008 | mild dementua (AS),Angina |
| DC-003 | 74 | F | 0 | 28.097 | 0.010 | severe dementia (AS) |
| DC-004 | 52 | M | 0 | 5.831 | 0.003 | VaD |
| DC-005 | 61 | F | 0.007 | 6.220 | 0.016 | FTD, progressive speech problem |
| DC-006 | 75 | M | 0.015 | 5.261 | 0.011 | VaD, Hypothyroidism |
| ADH-009 | 86 | F | 0.009 | 4.386 | 0.02 | Dementia – type unknown |
| ADH-037 | 78 | M | 0.008 | 10.585 | 0.042 | LBD |
| AD-042 | 78 | M | 0.001 | 8.146 | 0.015 | 16 moderate VaD |
| AD-069 | 86 | F | 0.002 | 15.731 | 0.015 | 25 mild VaD |
| AD-078 | 56 | M | 0.004 | 17.589 | 0.010 | 21 mild FTD |
| AD-082 | 72 | F | 0.017 | 24.562 | 0.019 | 26 mild MCI |
| AD-084 | 51 | F | 0.011 | 10.515 | 0.006 | 4 severe FTD |
| AD-086 | 67 | F | 0.025 | 32.101 | 0.013 | 20 mild CBD |
| Specificity | | | 93 % | 50 % | 93 % | |

MCI : mild cognitive impairment, CBD : corticobasal degeneration, FTD : fronto-temporal dementia, VaD : vascular dementia
LBD or DLBD : dementia with Lewy bodies

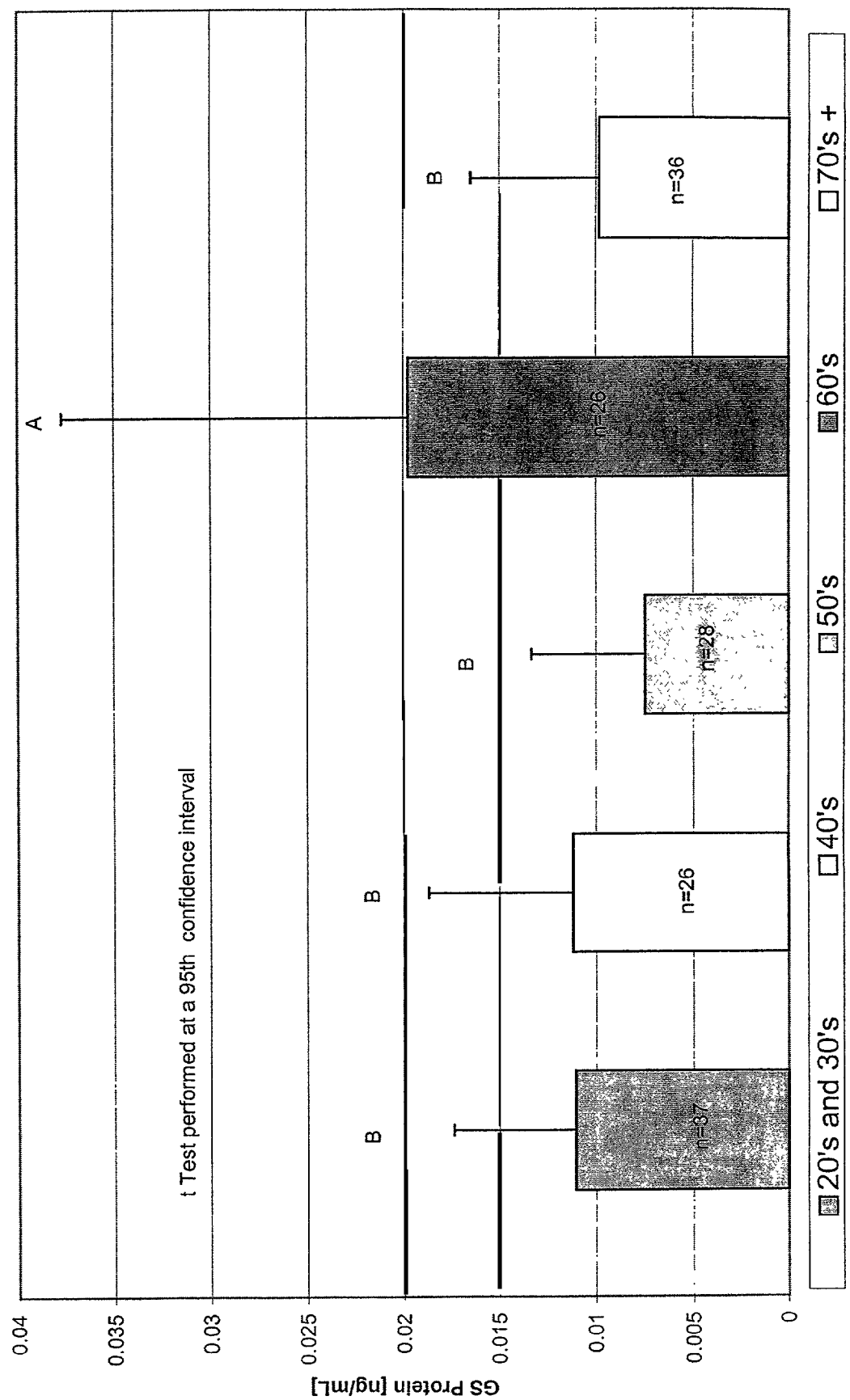

METHOD FOR DETECTING THE PRESENCE OF MONOMERIC BRAIN ASSOCIATED HUMAN GLUTAMINE SYNTHETASE

REFERENCE TO RELATED APPLICATIONS

This application is a continuation of Ser. No. 09/842,079, filed Apr. 25, 2001, now U.S. Pat. No. 6,451,547 the contents of which are herein incorporated by reference.

FIELD OF THE INVENTION

The present invention relates to a method for the diagnosis of Alzheimer's dementia (AD). The invention particularly relates to a process for quantifying the presence of at least one biochemical marker associated with Alzheimer's dementia. More particularly, the invention relates to a point-of-care immunoassay which utilizes unique antibodies to enable the differential diagnosis of Alzheimer's versus non-Alzheimer's forms of dementia.

BACKGROUND OF THE INVENTION

Alzheimer's disease, also referred to as Alzheimer's dementia or AD is a progressive neurodegenerative disorder that causes memory loss and serious mental deterioration. Diagnosticians have long sought a means to definitively identify AD during the lifetime of demented patients, as opposed to histopathological examination of brain tissue, which is the only present means available for rendering an ultimate diagnosis of AD. AD is the most common form of dementia, accounting for more than half of all dementias and affecting as many as 4 million Americans and nearly 15 million people worldwide. Dementia may start with slight memory loss and confusion, but advances with time reaching severe impairment of intellectual and social abilities. At age 65, the community prevalence of AD is between 1–2%. By age 75, the figure rises to 7%, and by age 85 it is 18%. The prevalence of dementia in all individuals over age 65 is 8%. Of those residing in institutions, the prevalence is about 50%, at any age.

The social impact of this disease is enormous, caused by the burden placed on caregivers, particularly in the latter stages of the disease. The substantial economic costs are largely related to supportive care and institutional admission. The rapidly increasing proportion of elderly people in society means that the number of individuals affected with AD will grow dramatically, therefore finding an early accurate diagnosis and a cure for AD is becoming an issue of major importance world wide.

When an individual is suspected of AD, several recommended tests are performed : (1) Mini Mental State Examination (MMSE)—an office-based psychometric test in the of a Functional Assessment Questionnaire (FAQ) to examine the scale for functional autonomy, (2) Laboratory tests—complete blood count, measurement of thyroid stimulating hormone, serum electrolytes, serum calcium and serum glucose levels, (3) Neuroimaging—most commonly used is computed tomography (CT) which has a role in detecting certain causes of dementia such as vascular dementia (VaD), tumor, normal pressure hydrocephalus or subdural hematoma. However, neuroimaging is less effective in distinguishing AD or other cortical dementias from normal aging. In primary care settings, some suggest that CT could be limited to atypical cases, but others recommend routine scanning. Magnetic resonance imaging (MRI) currently offers no advantage over CT in most cases of dementia.

While Alzheimer's is the most common form of dementia, accounting for at least 60% of cases, diagnostic procedures for determining the exact cause of dementia, among more than 80 different species, is difficult at best. Furthermore, the currently performed tests are inadequate in differentiating AD from other types of dementia.

In comparison to other disease areas, the field of dementia raises questions concerning the value of diagnosis, since there is currently no cure or effective therapy available. In dementia, as in all other branches of medicine, the certainty of a diagnosis has an important impact on the management of the patient. While AD cannot be cured at present time, there is symptomatic treatment available and the first drugs (acetylcholinesterase inhibitors) for the temporary improvement of cognition and behavior are now licensed by the U.S. Food and Drug Administration. Other drugs are at different stages of clinical trials: (1) Drugs to prevent decline in AD—DESFERRIOXAMINE, ALCAR, anti-inflammatory drugs, antioxidants, estrogen, (2) Neurotrophic Factors: NGF, (3) Vaccine: the recent most exciting report by Schenk et al. (Nature 1999;400:173–7) raises the hope of a vaccine for AD.

The specificity of the various therapies thus require sophisticated diagnostic methodologies, having a high degree of sensitivity for AD, in order to insure their success.

Currently there are a multitude of tests available which aid in the diagnosis of AD. However, the only true existing diagnosis is made by pathologic examination of postmortem brain tissue in conjunction with a clinical history of dementia. This diagnosis is based on the presence in brain tissue of neurofibrillary tangles and of neuritic (senile) plaques, which have been correlated with clinical dementia. Neuritic plaques are made up of a normally harmless protein called amyloid-beta. Before neurons begin to die and symptoms develop, plaque deposits form between neurons early on in the disease process. The neurofibrillary tangles are interneuronal aggregates composed of normal and paired helical filaments and presumably consist of several different proteins. The internal support structure for brain neurons depends on the normal functioning of a protein called tau. In Alzheimer's disease, threads of tau protein undergo alterations that cause them to become twisted. The neurohistopathologic identification and counting of neuritic plaques and neurofibrillary tangles requires staining and microscopic examination of several brain sections. However, the results of this methodology can widely vary and is time-consuming and labor-intensive.

Given the ability of both current and prospective pharmacological therapies to forestall and/or reverse the onset and/or progress of Alzheimer's dementia, an early diagnosis of AD will assist to better manage the care of patients. There are many cases where non-AD dementia could be confused with AD dementia. Such examples include small, undetected strokes which temporarily interrupt blood flow to the brain. Clinically depressed patients or those with Parkinson's disease can also experience lapses in memory. Many older people are on a variety of medications which as a side effect may, alone or in conjunction, impair their ability to perform cognitive tasks.

Thus, if diagnostic techniques for the early differentiation of AD could be provided, physician's would achieve an enhanced ability to prescribe appropriate therapeutic intervention at an early stage in the pathogenesis of this disease.

Various biochemical markers for AD are known and analytical techniques for the determination of such markers have been described in the art. As used herein the term "marker" "biochemical marker" or "marker protein" refers to any enzyme, protein, polypeptide, peptide, isomeric form thereof, immunologically detectable fragments thereof, or other molecule that is released from the brain during the course of AD pathogenesis. Such markers include, but are not limited to, any unique proteins or isoforms thereof that are particularly associated with the brain.

Glutamine synthetase (GS) is recognized as an astrocyte-specific enzyme involved in the regulation of ammonia and glutamate metabolism that is over-expressed following brain injury (Norenberg and Martinex-Hernandez, Brain Res 1979;161:303). A few studies on the clinical role of glutamine synthetase have been reported: Gunnersen and Haley (Proc Natl Acad Sci USA 1992;89:11949) found monomeric GS protein in 38 of 39 AD cerebrospinal fluid (CSF) samples, Tumani et al. (Arch Neurol 1999;56(10): 1241) describe that the concentration of GS in lumbar CSF of patients with AD is increased significantly but nonspecifically (i.e. also increased in VaD, schizophrenia and ALS). On p.1244, the left-hand column, Tumani states that GS was not found in serum.

Neuron-specific gamma-enolase (NSEγγ) and S1OOB proteins, abundant in the brain, are also useful markers for assessing the extent of brain damage: NSEγγ for neuronal damage and S100B for astrocyte damage. Concentrations of NSE and S100B proteins from cerebrocortical regions have been examined by means of enzyme linked immunosorbent assay (ELISA). The levels of these proteins in frontal cortex of AD patients were found to be significantly elevated (Kato et al. J Mol Neurosci, 1991;3(2):95). Activated astrocytes over-expressing S100B have been intimately associated with the neuritic β-amyloid plaques of AD (Sheng et al. J Neurosci Res, 1994;39:398, Mrak et al. J Neuropathol Exp Neurol 1996;55:273).

There are a number of different potential uses for biomarkers in AD evaluation, and each use could involve a different marker or set of markers. Such uses may include, but are not limited to, the use of a marker to distinguish AD from other causes of dementia; distinguishing dementia from the non-pathological effects of aging; monitoring the progress of the disease after clinical symptoms become apparent; utilization of a surrogate to monitor the efficacy of the forthcoming therapies for AD; and isolating markers which have utility as risk assessment factors for AD; and identifying both the earliest biological changes occurring in the brain and other changes that occur as the disease progresses. Ideally, it would be preferable to isolate a single marker to fulfill all requirements with a high degree of sensitivity and specificity, however this may be an unreasonable goal. Any individual marker needs to be assessed by sensitivity, specificity, reliability and validity for the type of clinical situation to which it is meant to apply. A marker which is poor at distinguishing AD from other causes of dementia, could nevertheless be an excellent marker for monitoring the progression of the disease process or the response to therapy.

With regard to diagnostic devices, the clinical evaluation and use of point-of-care tests utilizing biological markers are valuable tools for evaluating risk, monitoring disease progression and guiding therapeutic interventions. The advantages which flow from the use of biological markers as diagnostic tools include strengthening the certainty of the clinical diagnosis, distinguishing AD from other causes of dementia, and quantifying the severity of the disease and rate of progression. In addition, tests using biological markers should be rapid, non-invasive, simple to perform and inexpensive.

What is lacking in the art is a relatively non-invasive method and device therefore effective for definitively diagnosing Alzheimer's dementia in living patients. Additionally, a definitive method of assessing the risk of developing AD is greatly needed.

DESCRIPTION OF THE PRIOR ART

U.S. Pat. No. 5,445,937 to Haley teaches a method for the diagnosis of Alzheimer's disease, as well as a means for the diagnosis and differentiation of other diseases. This is done by use of a disease-specific biochemical marker, glutamine synthetase (GS) and its respective photoaffinity label, or labeled antibody specific for GS, at GS's binding site. The '937 patent focuses on examining cerebrospinal fluid (CSF) to detect the presence of a photoaffinity labeled, or labeled antibody, nucleotide binding protein and correlates the subsequent level with the presence of AD. Haley teaches a variety of immunoassay techniques to accomplish such a method. While Haley hypothesizes regarding the prophetical utility of diagnostic methods which use blood as a sample and further suggests that a monoclonal and/or polyclonal antibody immunoassay could be developed, he nevertheless fails to reduce either to practice. Thus, the '937 patent is only useful in teaching a diagnostic test which utilizes cerebrospinal fluid. Obtaining a sample of cerebrospinal fluid entails invasive techniques quite uncomfortable to a patient and requires a lengthy period of time to accomplish. In addition, the only polyclonal and/or monoclonal antibodies suggested by Haley are those having a specificity to sheep brain GS as opposed to a human recombinant form of GS as instantly disclosed herein.

In U.S. Pat. No. 5,508,167, Roses et al. describe methods for diagnosing AD involving the detection of an apolipoprotein E type 4 (ApoE4) isoform or DNA encoding ApoE4. The methods can use blood samples and are analyzed by an immunochemical assay. The blood sample is optionally combined with a reducing agent to reduce the disulfide bond in cysteine residues to the corresponding reactive sulfhydryl groups. Roses et al. further describes a kit for detection of the ApoE4 isoform. The test is based on the differences in the amino acid sequences of the three major ApoE isoforms. The test is not specific for human GS nor does it have sensitivity in differentially diagnosing AD versus non-AD dementia. Tumani et al. (Arch. Neurol., (1999) 56, pp1241–1246) examine the levels of GS in CSF and the examination of serum in order to determine whether GS is a useful biochemical marker in the diagnosis of AD. Analysis is by an ELISA utilizing a biotin-labeled monoclonal antibody directed against sheep brain GS. Normal ranges of GS concentration are reported as 4 pg/mL in human CSF and 36 pg/mL in human serum. The samples of CSF in AD patients are elevated with a mean level of GS concentration of 20±12 pg/mL, with ALS patients at 13±13 pg/mL, and vascular dementia (VaD) patients at a mean elevated level 13±7 pg/mL. Vascular dementia and ALS patients show a slightly lower increase. Patients with AD are measured with mean levels of 111±53 pg/mL in serum. However, patients with amyotrophic lateral sclerosis (ALS) and vascular dementia also present with mean elevated levels at 116±62 pg/mL and 72±59 pg/mL in serum, respectively. Thus, no definitive diagnosis regarding AD dementia or differential diagnosis between AD versus non-AD dementia could be elucidated from these assays.

Gunnersen and Haley (Proc. Natl. Acad. Sci. (1992) 89, pp11949–11953) provides evidence of GS detected in CSF of patients with AD but not in that of healthy control subjects or controls with other diseases. The other diseases under consideration are epilepsy, ALS, and Parkinson's. Patients with ALS or Pick's disease in addition to AD do show positive results, meanwhile ALS patients do not show positive results, indicating GS is specific to AD. As with other publications, antibodies raised against non-human GS are utilized for detection of GS.

Generally, most scientific papers tend to focus on the peptide, β-amyloid, since it is postulated to be a major determinant of AD. This is supported by the observation that certain forms of familial AD mutations result in the over production of β-amyloid, particularly the longer form (1–42) which aggregates more readily than the shorter form. Hensley et al. (Proc. Natl. Acad. Sci., (1994), 91, pp3270–3274) examine the neurotoxicity based on free radical generation by the peptide β-amyloid in its aggregation state. Several synthetic fragments of the peptide are tested for resulting neurotoxicity. Based on the fact that oxygen seems to be a requirement for radical generation and glutamate synthetase and creatine kinase enzymes are oxidation-sensitive biomarkers, the inactivation of these enzymes are utilized as indicators of active attack on biological molecules by these fragmented β-amyloid aggregates.

SUMMARY OF THE INVENTION

The present invention relates to a method for the diagnosis of Alzheimer's dementia (AD), particularly to a method for diagnosing and differentiating Alzheimer's dementia from other forms of dementia by testing for the presence of specific biochemical markers for Alzheimer's disease in bodily fluids, particularly in blood, blood products, urine, saliva and the like. The invention further relates to a process for quantifying the presence of at least one biochemical marker associated with Alzheimer's dementia. More particularly, the invention relates to a point-of-care immunoassay which utilizes unique antibodies to enable the differential diagnosis of Alzheimer's versus non-Alzheimer's forms of dementia.

The present invention relates to methods and ELISA system for diagnosing, subtyping and monitoring Alzheimer's disease. The invention is based on the discovery that S100B, NSEγγ and GS proteins are released from the brain and can be detected in body fluids outside the brain.

The generation and purification of recombinant human GS are described. These GS proteins may be used to generate monoclonal or polyclonal antibodies that, in turn, can be used in immunoassays, wherein they enter into an immunoreaction which can be monitored and/or quantified to detect circulating GS protein in suspected individuals. Alternatively, the GS protein themselves may be used in immunoassays to detect circulating autoantibodies in such individuals. The occurrence of Alzheimer's dementia is characterized by the recognition of levels of a particular biochemical marker in bodily fluid, said levels correlating to the manifestation of Alzheimer's dementia symptoms as quantified by MMSE testing. As a risk assessment test, the recognition of levels of such markers which are indicative of the development of Alzheimer's dementia further augments the diagnostic capability afforded to the skilled practitioner.

Accordingly, it is an objective of the instant invention to provide a relatively non-invasive and highly sensitive method for the definitive diagnosis of Alzheimer's disease.

It is a further objective of the invention to provide a method which includes analysis of at least one body fluid of a patient to determine the presence of at least one marker indicative of AD vs non-AD dementia.

It is a further objective of the instant invention to provide antibodies specific to neuronal related proteins, as identified by the method of the current invention.

It is a still further objective of the instant invention to provide an immunoassay effective for the recognition of neuronal specific proteins in one or more human bodily fluids.

It is yet another objective of the instant invention to provide a purified monoclonal antibody specific for human glutamine synthetase.

It is a still further objective of the invention to provide a test kit for the diagnosis of AD comprising a non-invasive point-of-care test which can be performed utilizing a sample comprising blood or any blood product.

Other objects and advantages of this invention will become apparent from the following description taken in conjunction with the accompanying figures wherein are set forth, by way of illustration and example, certain embodiments of this invention. The figures constitute a part of this specification and include exemplary embodiments of the present invention and illustrate various objects and features thereof.

BRIEF DESCRIPTION OF THE FIGURES

FIG. 1 is a comparison of statistically significant values for GS, NSE and S100 in the blood of a cohort of patients clinically evaluated as suffering from a form of Alzheimer's dementia;

FIG. 2 is a comparison of statistically significant values for GS, NSE and S100 in the blood of a cohort of patients clinically evaluated as suffering from a form of non-Alzheimer's dementia;

FIG. 3 depict box whisker plots of GS relative to age in healthy individuals.

DETAILED DESCRIPTION OF THE INVENTION

The markers which are analyzed according to the method of the invention are released into the circulation and may be present in the blood or in any blood product, for example plasma, serum, cytolyzed blood, e.g. by treatment with hypotonic buffer or detergents and dilutions and preparations thereof, and other body fluids, e.g. CSF, saliva, urine, lymph, and the like. In another preferred embodiment the concentration of the markers in CSF may be measured.

The terms "above normal" and "above cut-off" are used to refer to a level of a marker that is greater than the level of the marker observed in normal individuals who are not undergoing a cerebral event, i.e. brain degeneration or atrophy. For some markers, very low levels of the marker may be present normally in an individual's blood. For other markers analyzed according to the invention, detectable levels may be present normally in blood. Therefore, these terms indicate a level that is significantly above the normal level found in healthy individuals. The term "significantly" or "statistically significant" refers to statistical significance and generally means a two standard deviation (SD) above normal, or higher, concentration of the marker. The assay method by which the analysis for any marker protein is carried out must be sensitive to be able to detect the level of the marker which is present over the concentration range of interest and also must be highly specific.

The three markers which were compared to evaluate their value as a diagnostic tool are proteins which are released by specific cells in the brain as these cells become damaged during a cerebral event. These markers, e.g. proteins, can be either in their native form or they may be immunologically detectable fragments of the proteins resulting, for example, by proteolytic breakdown. By "immunologically detectable" is meant that the marker fragments contain an epitope which is specifically recognized by antibody reagents used in the assay.

The markers analyzed according to the method of the invention are cell type specific. The enzyme enolase catalyzes the interconversion of 2-phosphoglycerate and phosphoenolpyruvate in the glycolytic pathway. The enzyme exists in three isoproteins each the product of a separate gene. The gene loci have been designated ENO1, ENO2 and ENO3. The gene product of ENO1 is the non-neuronal enolase (NNE or α), which is widely distributed in various mammalian tissues. The gene product of ENO2 is the muscle specific enolase (MSE or β) which is localized mainly in the cardiac and striated muscle, while the product of the ENO3 gene is the neuronal specific enolase (NSE or γ) which is largely found in the neurons and neuroendocrine cells. The native enzymes are found as homo- or heterodimeric isoforms composed of three immunologically distinct subunits, α, β and γ. Each subunit (α, β and γ) has a molecular weight of 16 kDa, 44 kDa and 46 kDa respectively.

The αγ and γγ enolase isoforms, which have been designated as neuron specific enolase each have a molecular weight of ~80,000 Dalton. It has been shown that NSE concentration in CSF and blood increases after brain injury (e.g. stroke, head trauma), and the release of NSE from damaged cerebral tissue into the CSF and blood circulation reflects the extent of damage to cerebral tissue. NSE has a biological half-life of ~48 hours.

The S100 protein is a cytoplasmic acidic calcium-binding protein found predominantly in the gray matter of the brain, primarily in astroglial and Schwann cells. The protein exists in several homodimeric or heterodimeric isoforms consisting of two immunologically distinct subunits, A1 (MW 10,400 Dalton) and B (MW 10,500 Dalton). In the central nervous system (CNS), homodimer S100 B-B (21,000 Dalton) and heterodimer S100 A1-B (20,900 Dalton) constitute over 95% of the total S100 (Isobe et al. Biochem Int 1983;6:419, Zimmer et al. Brain Res Bull 1995;37:417). Since a high percentage of S100B is found in the brain, a number of studies have examined this protein as a marker of cerebral injury. The biological half life of S100B is 113 minutes (Usui et al. Clin Chem 1989;35:1942). Repeated measurements of S100B serum levels are useful to monitor the course of neurologic damage.

Glutamine synthetase (GS) is a ubiquitous enzyme that catalyzes the ATP-dependent conversion of glutamate to glutamine using ammonia as the nitrogen source. GS is present at high concentrations in liver, muscle, kidney and brain (De Groot et al. Biochim Biophys Acta 1987;908:231). GS in the human brain is an astrocyte-specific enzyme involved in protecting neurons via converting the potentially neurotoxic glutamate and ammonia into glutamine. The divalent cation site of GS renders it extremely sensitive to oxidation.

Senile plaque-dense regions of the brain of patients with AD represent environments of elevated oxidative stress and that protein in the brain of patients with AD is more oxidized than that of controls. Reactive microglia extensively present with senile plaque regions have been proposed as a source of oxyradicals in the brain.

Three distinct types of GS have been known: GSI, GSII and GSIII. Genes for GSI and GSIII have been found in bacteria. The human GS gene belongs to the GSII type (Brown et al. J Mol Evol 1994;38:566). GS in the brain is thought to exist as an octameric structure with a molecular weight of 360,000–400,000 Daltons (Tumani et al. J Immunol Meth 1995;188:155). However, in blood circulation the protein is thought to be in the monomeric form with MW 44±1 kDa (Boksha et al. J Neurochem 2000;75:2574). High concentrations of GS were reported in lumbar CSF from AD patients (Gunnersen and Haley, Proc Natl Acad Sci USA 1992;89:11949, Tumani et al. Arch Neurol 1999;56:1241).

The exact mechanisms leading to increased GS concentration in CSF remain unknown. Over expression of GS in reactive astrocytes and subsequent release into the extracellular space was proposed (Tumani et al, Arch Neurol 1999; 56:1241).

In a further contemplated embodiment of the invention, body fluid samples may be taken from a patient at one point in time or at different points in time for ongoing analysis. Typically, a first sample is taken from a patient upon presentation with possible symptoms of AD and analyzed according to the invention. Subsequently, some period of time after presentation, for example, about 3–6 months after the first presentation, a second sample is taken and analyzed according to the invention. The data can be used to diagnose AD, rule out AD, distinguish between AD and non-AD dementia.

The level of any one or all of the three specific markers of interest found in the patient's body fluid were measured from one single sample, although one or more individual markers can be measured in one sample. By "sample" is meant a body fluid such as blood or CSF. All the markers can be measured with one assay device or by using a separate assay device for each marker in which case aliquots of the same sample can be used. It is preferred to measure each of up to the three markers in the same single sample, irrespective of whether the analyses are carried out in a single analytical device or in separate devices so that the level of each marker simultaneously present in a single sample can be used to provide meaningful data.

The presence of each marker is determined using antibodies specific for each of the markers and detecting specific binding of each antibody to its respective marker. Any suitable direct or indirect assay method may be used, including those which are commercially available to determine the level of each of the specific markers measured according to the invention. The assays may be competitive assays, sandwich assays, and the label may be selected from the group of well-known labels such as radioimmunoassay, fluorescent or chemiluminescence immunoassay, or irumunoPOR technology. Extension discussion of the known immunoassay techniques is not required here since these are known to those of skill in the art. See Takahashi et al. (Clin Chem 1999;45(8):1307) for S100B assay.

Although not limited thereto, the immunoassay method used in the instant examples comprised a double antibody or sandwich ELISA for measuring the level of the marker proteins in the sample. According to this method, one of the antibodies is a "capture" antibody which is immobilized onto a solid-phase, and the other is a "detector" antibody which is labeled with, for example, an enzyme. The detector antibody binds to marker protein bound to the capture antibody to form a sandwich structure. For each assay of the three markers, marker protein standards are used to prepare a standard or calibration curve of absorbance vs marker protein concentration. This method is of importance since, in addition to the advantages of the preferred embodiment, the added markers, NSE and S100B, assist in indicating an on-going destruction of neurons and monitoring acute events in the brain, respectively.

The assay methods used to measure the marker proteins should exhibit sufficient sensitivity to be able to measure each protein over a concentration range from normal values found in healthy persons to elevated levels in sick people, i.e. 2SD above normal (=cut-off) and higher. For the GS protein, the cut-off=0.022 ng/ml, NSE=8.34 ng/ml and S100B=0.02 ng/ml.

The assay may be carried out in various formats, including a microtiter plate format which is preferred for carrying out the assays in a batch mode. The assays may also be carried out in automated analyzers which are well known in the art. Another assay format which can be used according to the invention is a rapid manual test which can be administered at the point-of-care at any location. Typically, such devices will provide a result which is above or below a cut-off, i.e. a semiquantitative result.

Expression of rhGS and Isolation of Monoclonal Antibody:

In order to isolate an antibody with specific binding properties for human Glutamine Synthetase (human recombinant GS or rhGS) cDNA of the rhGS was purchased from ATCC. The full length of the rhGS open reading frame (ORF) was obtained by PCR and sub-cloning in pET28a (NdeI/ShoI). The construct included a poly-histidine tag at the N-termini of the rhGS ORF and no extra sequence at the C-termini. The protein was expressed into *Escherichia coli* BL21 (DE3) following techniques described by Listrom et al. (Biochem J 1997;328:159). The preparation of crude cellular extract as well as solubilization of insoluble expression products consisting in urea/alkali treatment was achieved following the method of Moreno et al. (J Comp Neurol 1994;350:260). Affinity purification was performed by Ni-NTA chromatography following the supplier's recommendations.

Preparation of Monoclonal Antibody:

The monoclonal antibody of the present invention was produced by the polyethylene glycol (PEG) mediated cell fusion method.

Preparation of immunocytes: Balb/c mice, a strain with H-2$^d$ haplotype from Charles River Canada, St. Constant, Quebec, Canada, female, 7–9 week old, were immunized with the rhGS emulsified in an equal volume of either Freund's complete adjuvant (FCA) for the first injection and then in Freund's incomplete adjuvant (FIA) for subsequent injections at 2–4 weeks intervals with 25–100 µg of GS. Immunized mice were sacrificed 3–4 days after the final immunization, given either intravenously and/or intraperitoneally, in phosphate buffered saline buffer (PBS), pH 7.4.

Preparation of hybridoma: Spleen cells from the mice immunized with the GS protein and the Sp2/0 cells were fused in the presence of 42% PEG according to the method described by Fuller, S A, Takahashi, M and Hurrell, J G R (Preparation of Monoclonal Antibodies: In: Susubel F, Brent B, Kingston R., et al., eds. Current Protocols in Molecular Biology. New York: Greene Publishing Associates, 1987: Unit 11). The resulting fused cells were suspended in the HAT selection medium and plated onto four 96-well plates which were pre-seeded with feeder cells, peritoneal exudate cells (PEC), as described by Fuller et al. (see above reference).

Screening of GS-specific Antibody-secreting Hybridomas

The screening of hybridoma cultures were carried out in two methods. (1) Solid-phase ELISA—Screening ELISA-1: Confluent hybridoma culture supernatants were added to 96-well microtiter plates (NUNC MaxiSorp, GIBCO BRL) coated with rhGS at 2 µg/ml in 100 mM carbonate buffer, pH 9.6. The excess binding sites were blocked by bovine serum albumin (BSA) in PBS, pH 7.4. After washing the plate with PBS containing 0.05% Tween 20 (WB), 100 µL culture supernatants containing the monoclonal antibodies were incubated with the immobilized antigen for 1 hour at 37° C. After washing, peroxidase conjugated goat anti-mouse IgG (Jackson ImmunoResearch Lab, Inc., West Grove, Pa.) was added and incubated for 30 minutes at room temperature (RT) on a orbital shaker. After washing, TMB substrate solution (Sigma) was added. After 5 minutes incubation at RT in dark, the reaction was stopped with 1 M $H_2SO_4$ and optical density was read at 450 $_{nm}$. Selected positive cultures were subjected to cloning by the limiting dilution method as described by Fuller et al. (see above reference). ELISA screening and cloning procedures were repeated until culture stability and clonality were obtained. (2) Screening ELISA-2: In the second method, monoclonal antibodies in the hybridoma culture supernatant were captured via goat anti-mouse $IgG_{Fc}$ (Jackson ImmunoResearch) immobilized on the solid-phase of ELISA plate. After 1 hour incubation at 37° C., the plate was washed as for method-1. Then biotinylated GS (prepared using Biotin Labeling Kit from Boehringer Mannheim following the manufacturer's recommendation) diluted 1/2000 dilutions in PBS with 0.5% BSA was added to each well. After 30 minutes incubation at RT on a shaker, plate was washed and HRP-conjugated streptavidin (Boehringer Mannheim) at 1/10,000 was added and incubated for 30 minutes at RT. After washing, TMB substrate solution was added and reaction was read as for method-1.

To develop an ELISA assay, two clones designated as 1G3 and 5G4 were selected. These clones were deposited, in accordance with the Budapest Treaty, with the American Type Culture Collection, 10801 University Blvd., Manassas, Va. 20110-2209 on Apr. 25, 2001 under Accession Number PTA-3339 and PTA-3340 respectively. In accordance with 37 CFR 1.808, the depositors assure that all restrictions imposed on the availability to the public of the deposited materials will be irrevocably removed upon the granting of a patent.

Production of Monoclonal Antibody:

The GS-specific monoclonal antibody was produced using ascites. Ascites were produced in Balb/c mice previously treated with 0.25 ml pristane by injecting intraperitoneally with 1–5×10$^6$ hybridoma cells in 0.25–0.5 ml PBS, pH 7.4. Ten to 14 days later, ascites were collected. The monoclonal antibody from ascites was purified on affinity column (Protein G, AVIDAL), using known procedures. The purified monoclonal antibody was used for immunochemical studies.

Polyclonal Antibody Production and Purification:

Goats were immunized with biweekly 250–500 µg intramuscular and/or subcutaneous injections of purified rhGS emulsified in Freund's adjuvant. Titer was monitored routinely by screening serum by a half-sandwich ELISA. Polyclonal antibodies (PAb) specific for GS were subsequently purified from goat serum by affinity purification using cyanogen bromide activated SEPHAROSE-4B (Pharmacia)

coupled to recombinant GS. The purified polyclonal antibodies were dialyzed against 10 mM PBS, pH 7.4, concentrated by ultrafiltration and stored at −20° C.

Diagnostic Assays and Detection of GS in Biological Samples:

Another purpose of the present invention is to provide reagents for use in diagnostic assays for the detection of GS from individuals suffering from Alzheimer's disease.

In one mode of this embodiment, GS of the present invention may be used as antigens in immunoassays for the detection of those individuals suffering from AD. The protein, GS of the present invention may be used in any immunoassay system know in the art including, but not limited to: radioimmunoassay, enzyme-linked immunosorbent assay (ELISA), "sandwich" assays, precipitin reactions, gel diffusion immunodiffusion assay, agglutination assay, fluorescent immunoassays, protein A or G immunoassays and immunoelectrophoresis assays. According to the present invention, monoclonal or polyclonal antibodies produced against human GS are useful in an immunoassay on samples of blood or blood products such as serum, plasma or the like, spinal fluid or other body fluid, e.g. saliva, urine, lymph, and the like, to diagnose patients with AD. Alzheimer's dementia may be determined by utilizing a single monoclonal antibody or a plurality of monoclonal antibodies, singly or combined, which are specific against human glutamine synthasase.

The antibodies can be used in any type of immunoassay. This includes both the two-site sandwich assay and the single site immunoassay of the non-competitive type, as well as in traditional competitive binding assays.

Particularly preferred, for ease and simplicity of detection, and its quantitative nature, is the sandwich or double antibody assay of which a number of variations exist, all of which are contemplated by the present invention. For example, in a typical sandwich assay, unlabeled antibody is immobilized on a solid phase, e.g. microtiter plate, and the sample to be tested is added. After a certain period of incubation to allow formation of an antibody-antigen complex, a second antibody, labeled with a reporter molecule capable of inducing a detectable signal, is added and incubation is continued to allow sufficient time for binding with the antigen at a different site, resulting with a formation of a complex of antibody-antigen-labeled antibody. The presence of the antigen is determined by observation of a signal which may be quantitated by comparison with control samples containing known amounts of antigen.

Clinical Studies:

A prospective observational pilot study was carried out at three geriatric clinics. The study evaluated 38 patients who came to the clinic, wherein Mini Mental State Examination (MMSE) examination and other routine tests were given. Of those, 24 were diagnosed as AD and 14 with other types of dementia other than AD. The mean age of the patients presenting with Alzheimer's dementia was approximately 79 years with an age range of from 54 to 87 years. Mini Mental State Examination score (MMSE)was recorded. Blood sample was obtained, and after clotting, the sample was centrifuged and aliquots of serum were frozen and stored at 70° C. until analysis for S100, NSE and GS was performed.

Control subjects included 153 healthy blood donors (age range from 18–87 years: median age 71.03±9.95 years) whose blood samples were used to determine reference values for concentrations of S100, NSE and GS.

Alzheimer's disease is recognized as a progressive disease process which begins in the basal neocortex, spreads to the hippocampus, and eventually invades all cortical areas. There is no remission in the disease course (Braak and Braak, Neurobiol Aging 1997;18(4):351). This indicates that AD is a disease process and not simply a product of aging. AD pathogenesis involves steady and progressive destruction of neurons. Although NSE does not have specificity for AD, the marker contributes as an indicator of on-going destruction of neurons. Utilizing the monoclonal antibody instantly disclosed for human GS, an elegant, sensitive and specific assay for AD is made possible when the protein is analyzed in non-CSF bodily fluids. This is unlike prior art assays, wherein the markers were specific to nonhuman GS, and no definitive data could be derived from sera or any other non-CSF bodily fluid. S100 does not have the sensitivity, but it is a useful marker to monitor acute events in the brain (e.g. TIA, stroke, hypoxia leading to ischemic events, etc) which are common events among older individuals who are the target population of AD.

All reference values are reported as mean+2SD. The reference values for the three markers are: GS=0.022 ng/ml, NSE=8.34 ng/ml and S100=0.02 ng/ml.

The levels of S100 and NSE were analyzed using SMART S100 and SMART NSE ELISA assay kit, respectively, available from Syn-X Pharma Inc., Mississauga, Ont, CANADA. For the GS assay, antibody reagents and calibrator (i.e. recombinant human GS) were produced at Syn-X Pharma, and ELISA assay was developed as described above.

The box whisker plots in FIG. 3 depict the analysis of serum concentrations of GS protein in healthy individuals categorized on the basis of age. Interestingly, the individuals in their 60's show significantly higher levels of GS in blood in comparison to the other younger age groups. However, the mean GS level in blood of individuals 70+ go down similarly to those observed in their 20's and 40's. A similar pattern is observed with S100 protein. On the other hand, age distribution of NSE serum concentration is different from the other two markers in which significantly higher concentrations were observed in the age group of 14 to 40 years. There was no relationship of serum levels of these three proteins to sex. While not wishing to be bound by any particular theories, it was hypothesized that those in their 60's with elevated GS (and/or S100) are indeed already developing brain deterioration, and such individuals in their 70's become classified as "patients" and remaining so-called "healthy" individuals are well fit health-wise and show low levels of these protein markers. Thus, it was concluded that focusing upon GS levels in the 60's age group is especially valuable as a diagnostic for risk-assessment studies.

Of the 24 MMSE-based AD serum samples, 20 were mild AD cases, and 4 were moderate (See FIG. 1). The sensitivity of the three markers, i.e. GS, NSE and S100B were 100%, 33% and 8% respectively. The GS level correlates well with the severity of AD, i.e. MMSE score, while similar correlation is not observed with NSE. The sensitivity of S100 is very low, however, when this marker is elevated it may be an indication of ongoing destruction of astrocytes in the brain due to acute events.

Of the 14 non-AD dementia samples, only one sample shows an elevated level in both GS and S100, while 7 samples exhibit a concentration of NSE above the cut-off level (FIG. 2). This indicate GS and S100 to be highly specific markers for AD.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

One skilled in the art will readily appreciate that the present invention is well adapted to carry out the objects and obtain the ends and advantages mentioned, as well as those inherent therein. The oligonucleotides, peptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method for detecting monomeric brain associated human glutamine synthetase in a sample using a monoclonal antibody produced against human glutamine synthetase, whereby said monoclonal antibody is specific for monomeric brain associated human glutamine synthetase having a molecular weight of about 44 kDa, which comprises contacting the sample with the monoclonal antibody and detecting specific binding of the monoclonal antibody to monomeric brain associated human glutamine synthetase whereby said monomeric brain associated human glutamine synthetase in said sample is detected.

2. A method for detecting monomeric brain associated human glutamine synthetase in a sample using a monoclonal antibody encoded by the clone deposited with the ATCC as Accession Number PTA-3339, whereby said monoclonal antibody is specific for monomeric brain associated human glutamine synthetase having a molecular weight of about 44 kDa, which comprises contacting said sample with said monoclonal antibody and detecting specific binding of said monoclonal antibody to monomeric brain associated human glutamine synthetase whereby said monomeric brain associated human glutamine synthetase in said sample is detected.

3. A method for detecting monomeric brain associated human glutamine synthetase in a sample using a monoclonal antibody encoded by the clone deposited with the ATCC as Accession Number PTA-3340, whereby said nonoclonal antibody is specific for monomeric brain associated human glutamine synthetase having a molecular weight of about 44 kDa, which comprises contacting said sample with said monoclonal antibody and detecting specific binding of said monoclonal antibody to monomeric brain associated human glutamine synthetase whereby said monomeric brain associated human glutamine synthetase in said sample is detected.

* * * * *